United States Patent [19]

Lin

[11] Patent Number: 5,380,326

[45] Date of Patent: Jan. 10, 1995

[54] CLAMPING DEVICE FOR VERTEBRAL LOCKING ROD

[76] Inventor: Chih-I Lin, 513 S. Golden Pardos Dr., Diamond Bar, Calif. 10765

[21] Appl. No.: 151,016

[22] Filed: Nov. 12, 1993

[51] Int. Cl.⁶ ............................................. A61B 17/58
[52] U.S. Cl. .................................. 606/61; 606/72; 403/13; 403/374; 403/409.1
[58] Field of Search .............. 606/60, 61, 72, 73, 606/74; 403/13, 374, 409.1

[56] References Cited

U.S. PATENT DOCUMENTS

| | | | |
|---|---|---|---|
| 2,174,624 | 10/1939 | Donald et al. | 403/409.1 |
| 4,887,596 | 12/1989 | Sherman | 606/61 |
| 5,257,993 | 11/1993 | Asher et al. | 606/72 |
| 5,261,912 | 11/1993 | Frigg | 606/61 |

FOREIGN PATENT DOCUMENTS 4107480  9/1992  Germany ............................. 606/61

Primary Examiner—Tamara L. Graysay
Attorney, Agent, or Firm—Bacon & Thomas

[57] ABSTRACT

A clamping device for a vertebral locking rod includes an outer clamping member and an inner clamping member. The outer clamping member has a U-shaped clamping mount provided respectively in both inner sides thereof with a fitting member, with at least one of the two inner sides having a retainer. The inner clamping member has an arcuate fastening mount and a fastening block provided respectively in both outer sides thereof with a fitting member engageable with the fitting member of the outer clamping member. The arcuate fastening mount and the U-shaped clamping mount are joined together to form a retaining hole to hold therein a vertebral locking rod. The fastening block is provided in at least one of the two outer sides thereof with a retainer engageable with the retainer of the U-shaped clamping mount of the outer clamping member so as to prevent the fastening block from sliding in the U-shaped clamping mount.

4 Claims, 2 Drawing Sheets

CLAMPING DEVICE FOR VERTEBRAL LOCKING ROD

FIELD OF THE INVENTION

The present invention relates generally to an orthopedic device, and more particularly to a clamping device for a vertebral locking rod.

BACKGROUND OF THE INVENTION

The vertebral locking and retrieving system is generally composed of vertebral locking devices such as vertebral fastening nails, hooks sold under the trademark LUGUE and the like. These locking devices must be united with the vertebral locking rod in order to work effectively. A brief review of techniques relating to the fastening of the locking devices with the vertebral rod is in order. There are several conventional fastening methods, such as the nut and bolt fastening system, the lateral screw fastening system, the upper nut and bolt fastening system, the three-point shear clamp mechanism introduced by the DANEK Corporation of the United States, the V-groove connection design, sold under the trademark ISOLA and the spherical universal joint fastening system. According to the conventional technique, the locking devices, such as vertebral nails. LUGUE hooks and the like, are fastened with the vertebral locking rod by means of nuts and bolts. The nut-and-bolt method is defective in that the nut and the bolt are vulnerable to becoming loosened, and that the screwing of the nut onto the bolt is often a time-consuming task which prolongs the surgical operation. With a view to overcoming the shortcomings of the conventional technique described above, the Zimmer Corporation of the United States introduced a system, sold under the trademark MODULOCK system which employs the snap lock method. However, the MODULOCK system has an inherent drawback in that its constituent parts are provided with openings, which can be caused to become wider by the engaging force of the constituent parts of the MODULOCK system and the vertebral locking rod. In addition, the MODULOCK system is further defective in design in that its constituent parts are fastened indirectly with the vertebral locking rod by means of the intermediate snap rings. As a result, the fastening effect of the MODULOCK system is seriously undermined.

SUMMARY OF THE INVENTION

It is therefore the primary objective of the present invention to provide a closed clamping device of a ring-shaped construction, which serves to overcome the shortcomings of both the conventional systems and the MODULOCK system.

It is another objective of the present invention to provide a clamping device with an outer clamping member and an inner clamping member, which are united directly with the vertebral locking rod.

The foregoing objectives of the present invention are attained by a clamping device, which comprises an outer clamping member and an inner clamping member. The outer clamping member has a U-shaped clamping mount provided respectively in both inner sides thereof with a fitting member, with at least one of the two inner sides having a retaining means. The inner clamping member has an arcuate fastening mount and a fastening block provided respectively in both outer sides thereof with a fitting member intended to fasten with the fitting member of the outer clamping member. The arcuate fastening mount and the arcuate portion of the U-shaped clamping mount are joined together to form a retaining hole of cylindrical construction. The retaining hole is used to hold therein a vertebral locking rod. The fastening block is provided in at least one of the two outer sides thereof with a retaining means, which is fastened with the retaining means of the U-shaped clamping mount of the outer clamping member so as to prevent the fastening block from sliding in the U-shaped clamping mount.

The foregoing objective, structures and functions of the present invention can be more readily understood by studying the following detailed description of the present invention in conjunction with the drawings provided herewith.

DETAILED DESCRIPTION OF THE INVENTION

Figure 1:
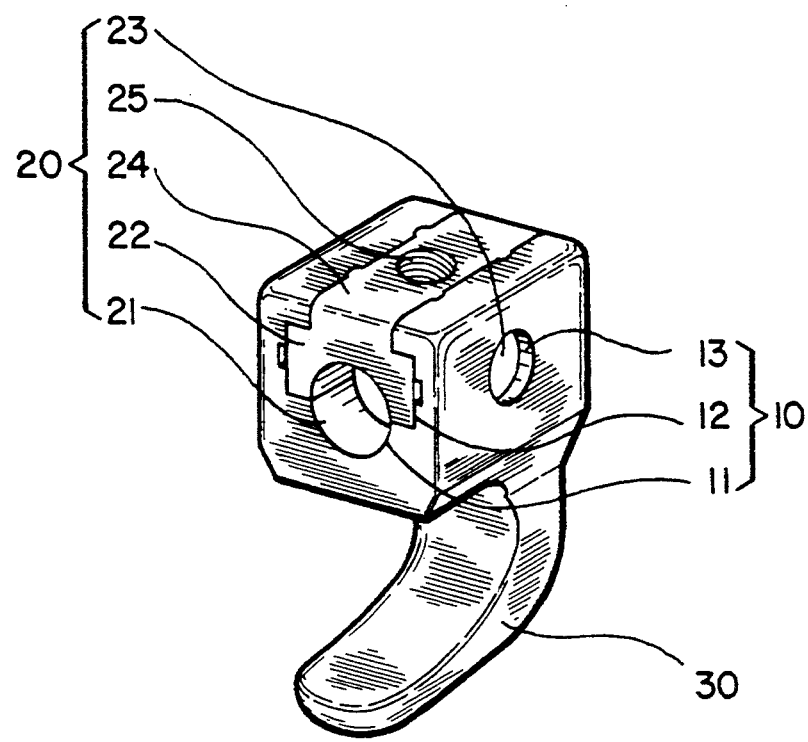
FIG. 1 shows a perspective view of a first preferred embodiment of the present invention.
Figure 1A:
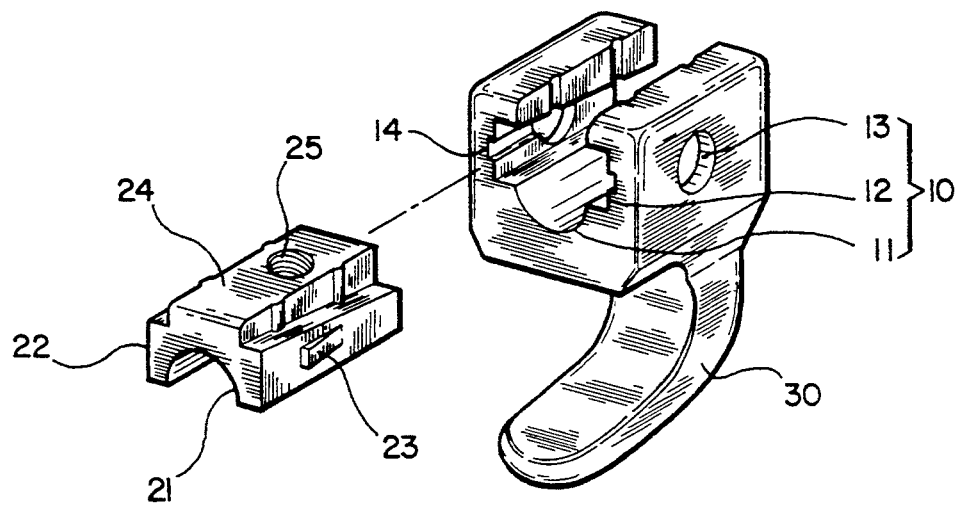
FIG. 1(a) shows an exploded perspective view of the first preferred embodiment of FIG. 1.

As shown in FIGS. 1 and 1(a), the clamping device of the present invention comprises an outer clamping member 10, an inner clamping member 20, and a LUGUE hook 30 integrally formed on the bottom surface of outer clamping member 10. The outer clamping member 10 is composed of a U-shaped clamping mount 11, a fitting slot 12 and a retaining hole 13. A groove 14 is provided on the surface of the fitting slot 12. The inner clamping member 20 is made up of an arcuate fastening mount 21, a fitting tenon 22, a retaining elastic protrusion 23, a clamping block 24, and a threaded hole 25 intended for use in fastening an auxiliary fixation device.

Figure 2:
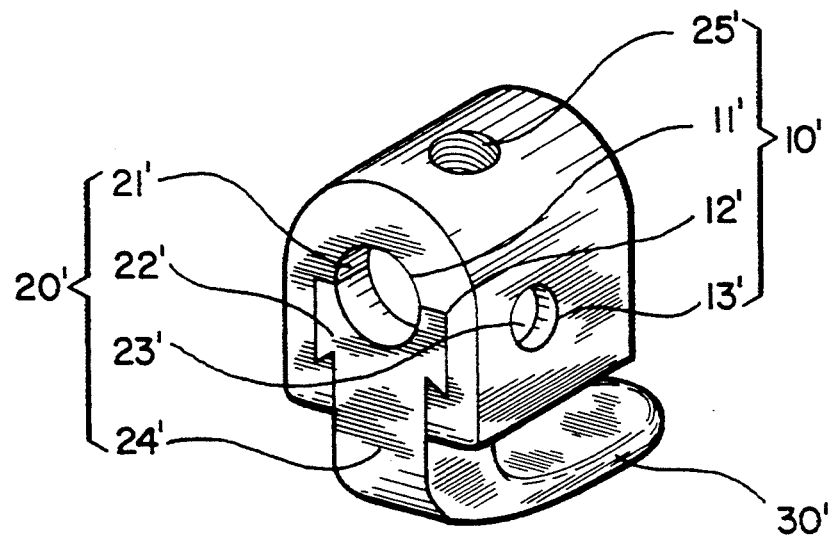
FIG. 2 shows a perspective view of a second preferred embodiment of the present invention.

The clamping device of the second preferred embodiment of the present invention is shown in FIG. 2 and all reference numerals are similar in definition to those of the first preferred embodiment of the present invention as shown in FIG. 1 are indicated with a prime. The clamping device of the second preferred embodiment differs from the first preferred embodiment in that the former comprises an outer clamping member 10' with a threaded hole 25' and and an inner clamping member 20' without a threaded hole and with a LUGUE hook 30'.

Figure 3:
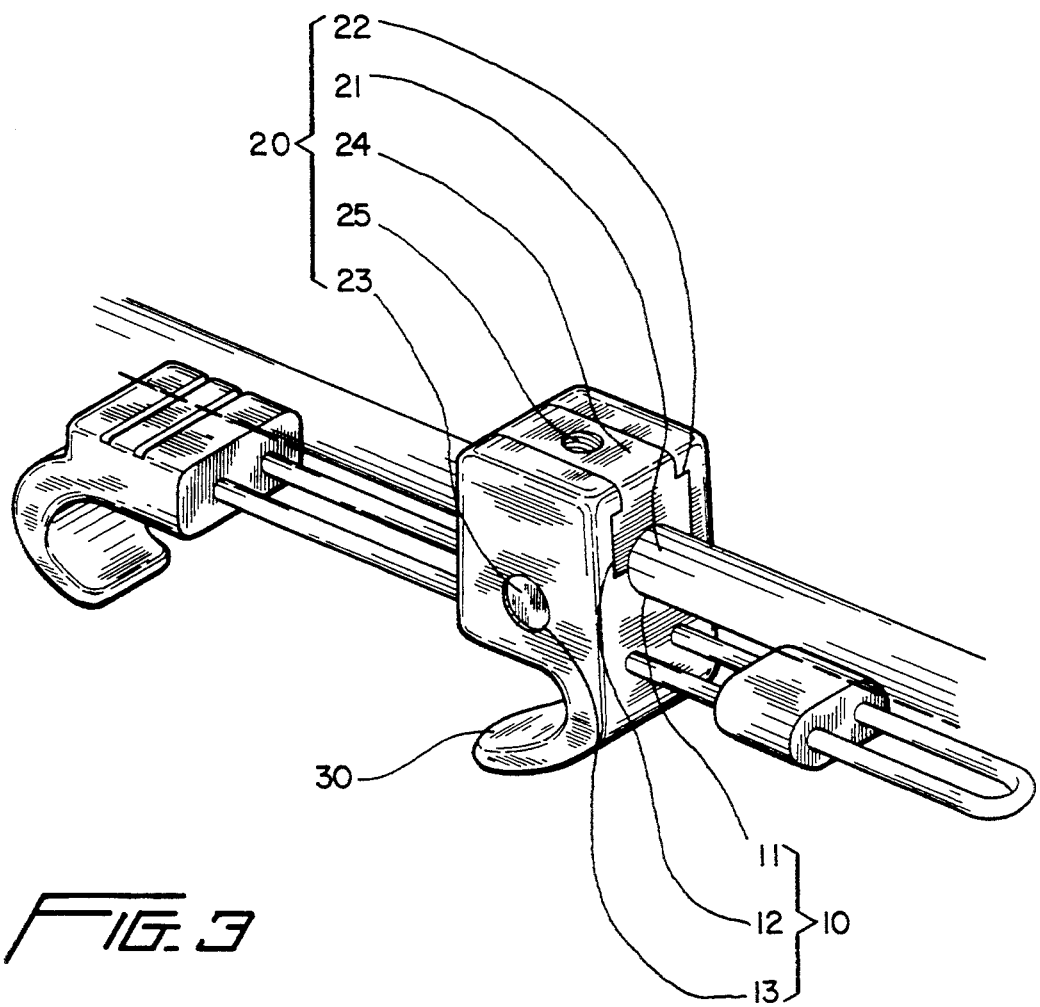
FIG. 3 shows a schematic view of the present invention cooperating with a vertebral locking and clamping device.

As shown in FIG. 3, the clamping device of the present invention is used in combination with a vertebral locking rod and the device disclosed by this inventor of present invention in a pending U.S. patent application Ser. No. 08/151,018 filed on Nov. 12, 1993. The reference numerals of FIG. 3 are similar in definition to those of FIG. 1.

It must be noted here that the Lugue hook used in the present invention may be replaced by a bone screw or other fixation devices such as a pedicle clamp and the device disclosed by this inventor of the present invention in the pending U.S. patent application Ser. No. 08/151,018 filed on Nov. 12, 1993. In addition, the threaded hole 25 of the first preferred embodiment of the present invention and the threaded hole 25' of the second preferred embodiment of the present invention are intended for use in fastening an auxiliary fixation system, such as a horizontal auxiliary fixation system.

The first preferred embodiment of the present invention comprises the outer clamping member 10 having a U-shaped interior which may be arranged variably in accordance with the surgical requirements. For example, the U-shaped interior may be an inverted U-shaped interior. The bottom portion of the U-shaped interior is so arcuate that it can cooperate with the profile of the vertebral locking rod. Similarly, the arcuate fastening mount 21 of the inner clamping member 20 is so constructed that it can cooperate with the arcuate profile of the vertebral locking rod. As a result, the outer clamping member 10 and the inner clamping member 20 can be joined together to form therebetween a retaining hole of cylindrical or oval construction and capable of retaining therein the vertebral locking rod. The retaining hole is progressively smaller in diameter from one end thereof toward another end thereof.

The outer clamping member 10 and the inner clamping member 20 are joined together such that the fitting tenon 22 of the inner clamping member is fitted into the fitting slot 12 of the outer clamping member 10. The fitting slot 12 and the fitting tenon 22 are similar in construction to any known mortise-tenon joint. In addition, the fitting slot 12 and the fitting tenon 22 may be of a wedge-shaped construction. Both the fitting slot 12 and the fitting tenon 22 are progressively smaller in dimension from one end toward another end thereof so that the inner clamping member 20 can joined together with the outer clamping member 10 in only one direction.

The outer clamping member 10 and the inner clamping member 20 are joined together securely by means of the retaining hole 13 of the outer clamping member 10 and the retaining elastic protrusion 23 of the inner clamping member 20 which is slid into the groove 14 until it engages the retaining hole 13 securely. Such a retaining technique as described above is similar to any known retaining method. Alternatively, a pair of vertical grooves may be provided on an inner side of the U-shaped clamping mount 11, and a pair of corresponding vertical protrusions may be provided on a side of the fitting block 24. In order to enhance the retaining effect, it is preferable that the inner clamping member is provided with the retaining elastic piece and that the outer clamping member is furnished with the retaining hole. If the inner clamping member is provided with the retaining hole instead of the retaining elastic piece, such retaining hole may be also used as a tool hole.

Either the outer clamping member 10 or the inner clamping member 20 may be fastened with a vertebral fixation device, such as a vertebral screw, or a LUGUE hook, etc. For instance, the outer clamping member 10 is fastened with the vertebral fixation device which is to be fastened onto the vertebra before the vertebral locking rod is retained in the U-shaped clamping mount 11 of the outer clamping member 10. Thereafter, the fitting tenon 22 of the inner clamping member 20 is first aligned with the fitting slot 12 of the outer clamping member 10 and is then moved in a sliding manner along the slightly inclined path to join with the fitting slot 12 such that the retaining hole 13 of the outer clamping member 10 engages securely the retaining elastic protrusion 23 of the inner clamping member 20. The clamping device of the present invention is able to clamp the vertebral fixation screw very well, in view of the fact that the fitting slot 12 and the fitting tenon 22 are provided respectively with a slight inclination, and that the retaining elastic protrusion 23 is of a tapered construction.

The clamping device of the present invention may be provided with a threaded hole for use in fastening a device such as an auxiliary fixation device.

The embodiments of the present invention described above are to be regarded in all respects as merely illustrative and not restrictive. Accordingly, the present invention may be embodied in other specific forms without deviating from the spirit thereof. The present invention is therefore to be limited only by the scope of the following appended claims.

What is claimed is:

1. A clamping device for a vertebral locking rod comprising:

an outer clamping member having opposing ends, said outer clamping member being formed with a U-shaped damping mount portion that is located between opposing inner sides of said outer clamping member and extends between the opposing ends of said outer clamping member, each of said opposing inner sides including an inclined fitting slot, at least one of said opposing inner sides at its inclined fitting slot being formed with a first retaining member; and an inner clamping member having opposing ends, said inner clamping member including opposing inclined fitting members and an arcuate fastening mount portion located between said fitting members, at least one of said fitting members being provided with a second retaining member, wherein said inner clamping member is adapted to be inserted in a predetermined direction and slidably positioned within said outer clamping member with each of said fitting members mating with a respective one of said fitting slots, said U-shaped clamping mount portion and said arcuate fastening mount portion defining a substantially cylindrical clamping hole adapted to receive a vertebral locking rod, and said first and second retaining members being interengaged to retain said inner clamping member within said outer clamping member.

2. The clamping device of claim 1, further including a vertebral fixation device carried by one of said inner and outer clamping members.

3. The clamping device of claim 2, wherein said first retaining member comprises a hole formed in the at least one of said opposing inner sides of said outer clamping member and said second retaining member comprises an elastic protrusion extending from the at least one of said fitting members, said elastic protrusion being adapted to project into said hole.

4. The clamping device of claim 3, wherein said elastic protrusion tapers in said predetermined direction.

* * * * *